(12) United States Patent
Van Den Brink et al.

(10) Patent No.: US 6,855,855 B2
(45) Date of Patent: Feb. 15, 2005

(54) AROMATICS ALKYLATION

(75) Inventors: Peter John Van Den Brink, Amsterdam (NL); Avelino Corma Canos, Valencia (ES); Edward Julius Creyghton, Amsterdam (NL); Vicente Fornes Segui, Valencia (ES); Vicente Martinez Soria, Valencia (ES)

(73) Assignees: Consejo Superior de Investigaciones Cientificas, Madrid (ES); Universidad Politecnica de Valencia, Valencia (ES)

( * ) Notice: Subject to any disclaimer, the term of this patent is extended or adjusted under 35 U.S.C. 154(b) by 0 days.

(21) Appl. No.: 10/102,512

(22) Filed: Mar. 20, 2002

(65) Prior Publication Data

US 2003/0004382 A1 Jan. 2, 2003

Related U.S. Application Data

(63) Continuation of application No. PCT/EP00/09255, filed on Sep. 20, 2000.

(51) Int. Cl.⁷ .................................. C07C 2/66
(52) U.S. Cl. ........................... 585/467; 585/906
(58) Field of Search .................. 585/467, 906

(56) References Cited

U.S. PATENT DOCUMENTS

| | | |
|---|---|---|
| 3,755,483 A | 8/1973 | Burress |
| 4,393,262 A | 7/1983 | Kaeding |
| 4,439,409 A | 3/1984 | Puppe et al. |
| 4,469,908 A | 9/1984 | Burress |
| 4,826,667 A | 5/1989 | Zones et al. |
| 4,891,458 A | 1/1990 | Innes et al. |
| 4,954,325 A | 9/1990 | Rubin et al. |
| 4,962,256 A * | 10/1990 | Le et al. ............... 585/467 |
| 5,149,894 A | 9/1992 | Holtermann et al. |
| 5,229,341 A | 7/1993 | Kresge et al. |
| 5,453,554 A | 9/1995 | Cheng et al. |
| 5,493,065 A | 2/1996 | Cheng et al. |
| 5,691,463 A | 11/1997 | Zones et al. |

FOREIGN PATENT DOCUMENTS

| | | |
|---|---|---|
| EP | 0293032 | 5/1988 |
| WO | WO 92/11934 | 7/1992 |
| WO | WO 97/17290 | 5/1997 |
| WO | WO 97/19021 | 5/1997 |

OTHER PUBLICATIONS

A Corma et al, Delaminated Zeolite Precursors as Selective Acidic Catalysts, Nov. 26, 1998, pp. 353–356.
O. Terasaki et al, What Can We Observe in Zeolite Related Materials by HRTEM?, (Catalysis Today 23) (1995) 201–218.
MWW (Framework Type) P6/mmm; pp. 202–203.
Webb et al; Analytical Methods in Fine Particle Technology; (1997) ISBN 0–9656783–O–X; p. 134.
Hydrocarbon Processing, Mar. 1999, Petrochemical Processes '99.

\* cited by examiner

*Primary Examiner*—Thuan D Dang
(74) *Attorney, Agent, or Firm*—Klauber & Jackson

(57) ABSTRACT

The invention provides a process for the alkylation of an aromatics compound with a olefin alkylation agent which comprises contacting the aromatic compound, especially benzene, with the alkylation agent, especially ethylene and/or propylene, in the presence of an oxide material which is delayered MWW-type zeolitic material, very suitably the material known as ITQ-2.

11 Claims, 2 Drawing Sheets

AROMATICS ALKYLATION

Figure 1:
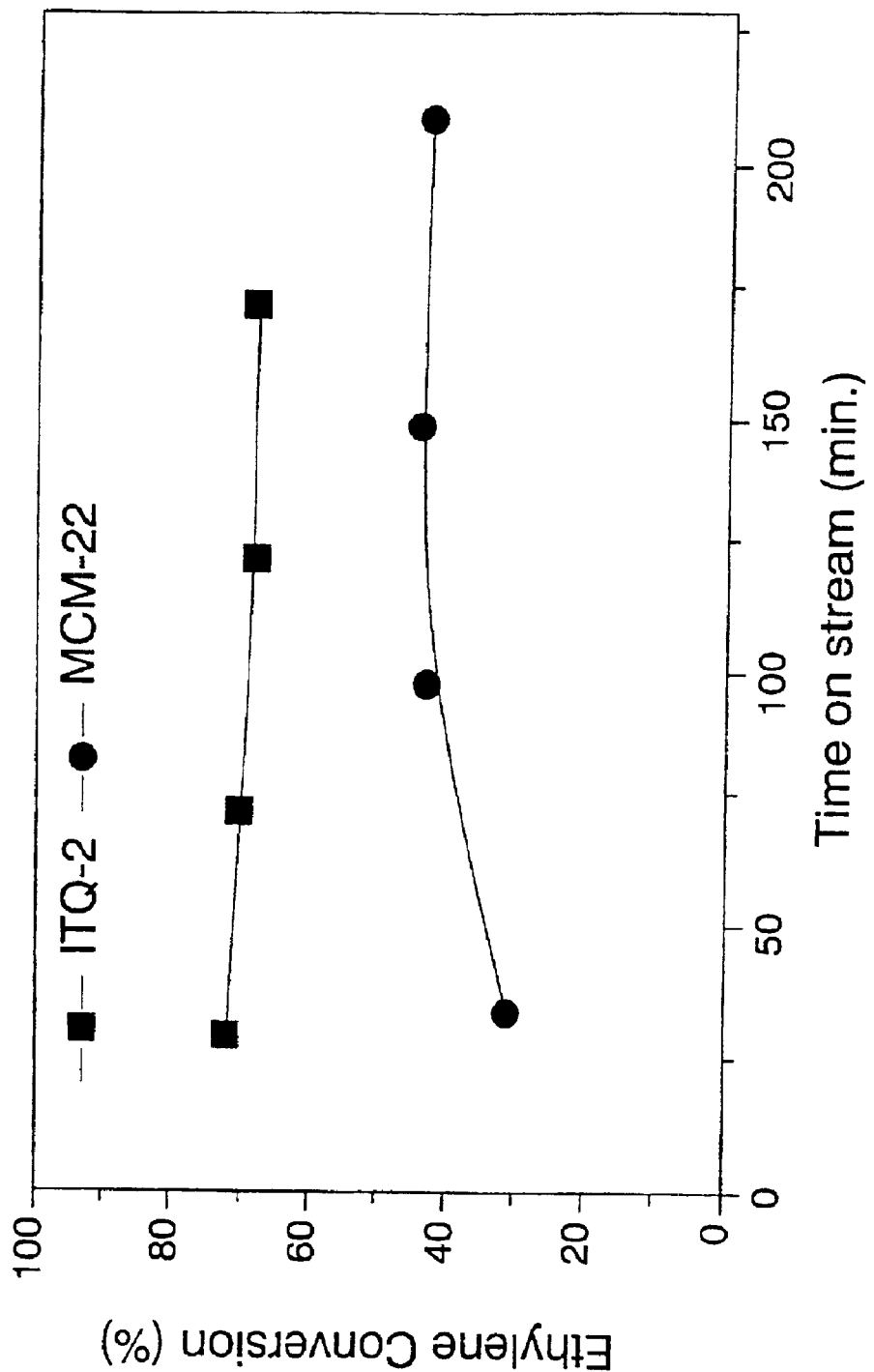

This application is a continuation of PCT/EP00/09255 filed Sep. 20, 2000.

The present invention concerns aromatics alkylation using zeolitic-related material.

Zeolites are microporous aluminosilicate crystalline materials having a uniform three dimensional structure. Because of their uniform crystalline structure they have found wide-ranging use in industry where shape selectivity is required or advantageous. Therefore zeolites are proposed for use inter alia as adsorbents, e.g. for purification, as catalysts for chemical and petrochemical processes, and as ion-exchangers, e.g. as water-softening agents.

Nomenclature for zeolitic materials is determined by the Structure Commission of the International Zeolite Association (IZA-SC) which has been given the authority by IUPAC to assign structure type codes to all unique and confirmed framework topologies. Currently the definitive terminology is recorded in the Atlas of Zeolite Structure Types (4th Edition, authors W. M. Meier, D. H. Olson and Ch. Baelocher, or accessible, in regularly updated form, on website www.iza-sc.ethz.ch/IZA-SC/Atlas/AtlasHome.html). This handbook logs the topology of each zeolite type deemed to be of new and independent structure and currently quotes some 125 independent zeolite structures.

Typically in zeolite synthesis the raw materials including primarily aluminium and silicon sources are reacted in an aqueous synthesis gel to form crystals, which when grown are dried and often calcined to remove water from the formed pores and provide the useful and distinctive porous structure. In recent times attempts have been made to design zeolitic materials by the use of organic structure directing agents (also known as templates) in the synthesis gel. These chemicals are used to ensure a particular pore size within a zeolite structure following drying and calcination, and thence removal of, inter alia, the template from the formed crystalline structure.

The zeolitic materials designated by the IZA-SC as being of the MWW topology are multi-layered materials which have two pore systems arising from the presence of both 10 and 12 membered rings. The Atlas of Zeolite Structure Types classes five differently named materials as having this same topology: MCM-22, ERB-1, ITQ-1, PSH-3, and SSZ-25. The zeolites of the MWW type are described as having varied uses. U.S. Pat. No. 4,826,667 describes zeolite SSZ-25 as useful primarily for catalyzed hydrocarbon conversion reactions, such as catalytic cracking, hydrocracking, hydrodewaxing, olefin and aromatics formation reactions such as xylene isomerisation, but also as an adsorbent, as a filler and as a water-softening agent. U.S. Pat. No. 4,954,325 lists 16 different uses for the material now known as MCM-22.

Aromatics alkylation is one such use. Many of the important alkyl aromatic compounds used for petrochemical intermediates are produced by alkylating benzene with monoolefins. The synthesis of ethylbenzene and of cumene are two commercially important examples. In the former benzene is catalytically converted to ethylbenzene with ethylene, in cumene production benzene is reacted with propylene. In particular most of the ethylbenzene required for styrene production is made synthetically. Prior to the advent of zeolites, such alkylation was carried out using a Friedel-Crafts type of catalyst such as aluminium chloride (in liquid phase alkylation) and boron trifluoride (in vapour phase alkylation) but these catalysts are corrosive and present operational, handling and disposal problems.

Many zeolites and zeolite-related materials have been proposed for aromatics alkylation (zeolite beta (U.S. Pat. No. 4,891,458), ZSM-5, ZSM-12 (U.S. Pat. Nos. 3,755,483, 4,393,262, 4,469,908), SSZ-25 (U.S. Pat. No. 5,149,894), MCM-49 (U.S. Pat. No. 5,493,065), MCM-36 (U.S. Pat. No. 5,229,341), MCM-56 (U.S. Pat. No. 5,453,554)) but few have actually proved of use commercially. Initially, acidic ZSM-5 catalysts were used and enabled vapour phase ethylbenzene production to be operated successfully on a commercial scale; zeolite Y has been used commercially in liquid phase cumene production; and currently MCM-22 is used in liquid phase ethylbenzene production, these are the few zeolites acknowledged to be used commercially (see Hydrocarbon Processing, March 1999, Petrochemical Processes '99, Ethylbenzene). None of the other MWW-type zeolites have apparently found commercial use in aromatics alkylation, nor have any of the closely related forms of MCM-22: MCM-49, commonly considered to be an at least partially template-filled form of MCM-22, MCM-36, which is a pillared form of MCM-22 prepared by pillaring swollen, layered MCM-22 precursor in order to increase the distance between the layers and so increase the catalytically active available surface area, or MCM-56, another multi-layered material related to MCM-22.

One of the reasons that few zeolites find use in commercial alkylation is that fouling or coking is a severe problem under industrial conditions, and the fine pores of zeolitic material can quickly become clogged or coked leading to rapid deactivation particularly with catalysts of high activity. Such fouling can come for example from deposition of oligomerised olefin reactant (particularly a problem with propylene) or deposition of other carbonaceous by-product material. Even the zeolites currently in commercial use need to be regularly regenerated and may be used in a "swing" system where two reactors are used so that processing and regeneration can operate in tandem without interrupting production—this is particularly the case with high temperature vapour phase alkylation to produce ethylbenzene. There continues to be a need in industrial aromatics alkylation for zeolite-type material that can combine a high activity with a prolonged catalyst life (i.e. a low coking tendency).

It has now been found that, in its calcined form, oxide material which is the delayered form of the MWW-type layered zeolites not only exhibits useful aromatics alkylation activity but also has increased activity and catalyst life over the most successful commercial alkylation catalyst of the MWW type, MCM-22.

Accordingly the present invention provides a process of alkylating an aromatic compound with an olefin alkylating agent which comprises contacting the aromatic compound with the olefin alkylating agent in the presence of calcined oxide material which is a delayered MWW zeolite.

Delayering of MWW zeolite may be achieved by delamination of the layered intermediate (formed from a synthesis gel including a structure directing agent), in which the layers are split apart before the drying or calcination stage which would set the layered material into a solid, multi-layered crystal structure. Normally for the MWW form of zeolite the layered intermediate has been swollen with a surfactant at a high pH (normally above 11); delamination therefore causes delayering of this swollen layered intermediate. For the SSZ-25 zeolites, the structure directing agent contains adamantane quaternary ammonium ions, and is e.g. the hydroxide. For the PSH-3, ERB-1 and MCM-22 zeolites the template material utilized is hexamethyleneimine. For ITQ-1 zeolite, the template material is a mixture of adamantane quaternary ammonium ions and hexamethyleneimine.

Where the template materials are of such significantly different molecular size then the layers of the layered intermediates when swollen become differently spaced apart depending on the molecular size (a smaller molecule allows a closer spacing, and a larger molecule a spacing which is further apart). As the X-ray diffraction patterns (XRD) of these materials detect the layers and their spacing, then use of a different template gives rise to a different XRD between intermediates. As can be concluded from the inclusion of the materials in the same topology type (MWW), however, the essential or characteristic pore structure of the individual layers should be the same.

The MWW-type zeolites and their intermediates have of the order of 10 layers in the zeolitic structure. A delayered MWW zeolite is to be understood herein as the material formed or obtainable when the characteristic multi-layered structure of an MWW zeolite precursor is broken up to give discrete fragments each of which contain substantially less than 5 layers; this can readily be assessed by the person skilled in the art of zeolite characterization. Delamination enables an oxide material to be prepared which is suitably, predominantly (50% or more) of single layer material, with the remaining material being of two or possibly three layers only, but still having the 10 and 12 ring systems characteristic of the MWW-type materials. Preferably at least 70% of the delaminated material is in the form of a single sheet or layer, and especially at least 90%.

This delamination technique and a very suitable delayered oxide material has been described in International Patent Specification No. WO 97/17290. The calcined oxide material is described therein as possessing channels formed by 10-membered atomic rings (termed 10 MR) having a pore diameter of 0.56 nm (5.6 Å) and chalice-shaped cavities that measure 0.8×0.7 nm (8×7 Å) which are open to the outside via 12-membered atomic rings (termed 12 MR), as indicated by a high adsorption capacity for the bulky molecule 1,3,5 trimethylbenzene (at least 0.50 mmol/g). The delaminated material was described especially for use in catalytic cracking of hydro-carbonaceous feedstocks. This material is now known as ITQ-2 (Nature, Vol. 396, 353–356, 26 Nov. 1998).

It is obtainable by a process which comprises, prior to calcination, at least partially delaminating a swollen layered oxide material having an X-ray diffraction pattern including values substantially as set forth in Table II below:

TABLE II

| d (Ångstrom) | Relative Intensity, $I/I_o \times 100$ |
| --- | --- |
| >32.2 | vs |
| 12.41 ± 0.25 | w-s |
| 3.44 ± 0.07 | w-s |

The delaminated material exemplified in WO 97/17290 had been prepared from swollen MCM-22 precursor and was compared against MCM-22 and found to have an increased surface area, a reduced Bronsted acidity and a similar or slightly increased Lewis acidity.

Delamination may be achieved by any technique that is capable of subjecting the layered swollen MWW-intermediate material to an adequately high stress at the molecular level to split the layers apart without damaging the microporous structure of the individual layers. Two examples of such techniques are ultrasonic disruption and high shear, high speed stirring (also termed hydrodynamic cavitation).

As noted above such calcined delaminated materials have already been shown to have increased activity for catalytic cracking over MCM-22. Catalytic cracking requires an acidic catalyst that can accommodate large molecules that are present in a mixed hydrocarbon feed but most particularly allow rapid exit of molecules once cracked. In this situation acidity is less important than a reduced diffusion path to avoid overcracking to the less useful gaseous hydrocarbons.

However to be commercially useful as an alkylation catalyst high acidity and improved catalyst life are both as important as catalytic site accessibility. It is to be expected that delaminated materials although providing an increased surface area, would have an equivalent catalyst life to the layered MWW materials through having a common internal 10 MR pore or channel system which would be subject to the same tendency to become blocked or coked from oligomerised byproducts or other side reactions. Additionally from the comparison of ITQ-2 and MCM-22 in WO 97/17290 the acidity level of the delaminated material is either less or at best similar to that of the multi-layered material, and therefore the level of alkylation activity would be expected also to be lower or of the same order in the delaminated material.

It has, however, surprisingly been found that in comparison with MCM-22, the delayered material ITQ-2, although of similar or lower acidity and having the same 10 MR microporous structure, exhibits a significantly higher activity for ethylbenzene production and for cumene production, and a longer catalyst life particularly for benzene-propylene conversion to cumene.

The delamination technique can be applied to a swollen, layered intermediate of any of the MWW-type zeolites. Such material is often termed "as-synthesized" material. These "as-synthesized" materials are suitably prepared as described in the literature; the synthesis of zeolite PSH-3 is described in U.S. Pat. No. 4,439,409, of ERB-1 in EP-A-293032, of SSZ-25 in U.S. Pat. No. 4,826,667, of ITQ-1 in WO 97/19021, and of MCM-22 in U.S. Pat. No. 4,954,325—additionally the swollen oxide intermediate of MCM-22 is described in WO 92/11934. Suitably, once the swollen intermediate has formed and the zeolite is in its "as-synthesized" state, delamination is then carried out. It is however also possible for the delamination to be performed on the synthesis mixture while the intermediate is being synthesized. Once delaminated the material is then dried and calcined to remove the organic materials and water and in order to set the oxide material into a solid form. It can be advantageous additionally to perform an acid treatment prior to drying and calcination, as described in WO 97/17290 to assist with flocculation of the delaminated solid.

The delayered material in its calcined form can be readily identified in its distinctive predominantly single layer structure of exposed, open chalice-shaped 12 MR cups and interconnecting 10 MR channels or pores, through TEM (transmission electron microscopy), very suitably HRTEM (high resolution transmission electron microscopy), see "What can we observe in zeolite related materials by HRTEM" by Terasaki and Ohsuna, Catalysis Today, 23 (1995), 201–218 and also by argon adsorption at low relative pressure ($P/P_O$), see Analytical Methods in Fine Particle Technology by Webb and Orr (1997), ISBN 0-9656783-0-X, section 3.6.7.2, page 134.

Preferably the delayered zeolitic material has a silicon to aluminium atomic ratio in the range of from 10 to 100, preferably 15 to 70, more preferably of from 20 to 70. Very useful aromatics alkylation activity has been shown by delayered materials having a silicon to aluminium atomic ratio of 50.

The term "aromatic" when used herein has its normal meaning in the art, and will be understood to include unsubstituted and substituted mono, di- or poly-nuclear compounds of aromatic character. Hetero atom containing aromatic compounds are also included. By "olefin alkylation agent", there is to be understood a monoolefin having from 2 to 22 carbon atoms; said olefins may be straight chain or branched chain compounds which may also have other functional groups, for example hydroxy groups provided they do not interfere with the alkylation process. Mixtures of alkylating agents such as are found in refinery gas streams are also included.

The process of the invention can very suitably be used for the preparation of a wide range of alkyl-substituted aromatics including alkyl-substituted benzenes, toluenes, xylenes, phenols (for example the alkylphenolic synthetic detergents), naphthalenes, naphthols, anthracenes, anthranols, and phenanthranols.

Most suitably however, the process finds use in the alkylation of benzene with a monoolefin of from 2 to 8 carbon atoms, more preferably from 2 to 4 carbon atoms, and especially in the alkylation of benzene with ethylene and/or propylene.

The alkylation process is suitably carried out at the conventional conditions of temperature and pressure as appropriate for the reactants, and generally this will be at a temperature in the range of from 0 to 500° C., a pressure in the range of from 20 to 25,000 kPa, a molar ratio of aromatics compound to alkylating agent of from 0.1:1 to 50:1, preferably at least 2:1, and a feed weight hourly space velocity (WHSV) of from 0.1 to 100, preferably from 0.5 to 20. The alkylation may be operated on a batch, semi-batch or continuous basis, continuous operation being the most preferred from a commercial viewpoint, and in a fixed bed, fluidized bed or moving bed vessel.

It is most preferred that the process be applied in the production of ethylbenzene and cumene. These alkylations are conventionally operated as either a vapour phase alkylation or as a liquid phase alkylation. The conventional operating conditions known in the art may be applied in each case.

Thus, vapour phase alkylation is normally carried out at a temperature in the range of from 350° C. to 500° C., preferably 370 to 450° C., combined with a pressure in the range of from 1 to 5 MPa, preferably 1.5 to 3 MPa, with a molar ratio of benzene to olefin alkylation agent in the range of from 1:1 to 25:1, preferably about 5:1. Such vapour phase alkylations are suitably carried out using at least two fixed bed swing reactors, each with one or more beds of alkylation catalyst, operating in tandem to allow simultaneous processing and catalyst regeneration. A very suitable process for the production of ethylbenzene is that known as the Mobil-Badger process which was developed and commercialized particularly for the use of ZSM-5.

It is most preferred that the alkylation process of the invention be applied for the production of ethylbenzene or especially of cumene in liquid phase alkylation. Liquid phase process systems can be operated for the production of either commodity, unlike vapour phase systems which have to be designed specifically for one of the two alkylated benzenes. Generally liquid phase systems operate at a temperature in the range of from 100 to 350° C., preferably 130 to 270° C., a pressure in the range of from about 2 to 6 MPa, preferably from 2 to 4 MPa, a molar ratio of benzene to olefin of 1:1 to 30:1, but preferably a ratio of from 2:1 to 10:1, and a WHSV of the order of from 0.1 to 20, preferably in the range of from 0.5 to 10. Liquid phase systems that are suitable for the alkylation process of the present invention are the conventional fixed bed systems and the more recent catalytic distillation system developed by the companies CR&L and CDTECH. Such systems usefully operate with a downstream transalkylation reactor utilizing a suitable transalkylation catalyst which produces additional desired product from isomeric by-products and so maximizes yield.

In catalytic distillation, reaction and separation operates at the same time normally in the same (distillation) vessel. For alkylation reactions catalytic distillation can actually be effected at low temperature and pressure using a single vessel and may usefully incorporate a second fractionator to operate with the reaction vessel as a distillation column. Thus for cumene production a single reaction/distillation system has been proposed in which alkylation occurs and the reaction products are continuously distilled off; this system actually operates as a mixed-phase system which requires a low propylene concentration in the liquid phase (less than 0.1 wt %) and minimizes propylene oligomerisation, a major cause of catalyst deactivation in cumene production. In ethylbenzene production, the catalytic distillation system currently proposed is a combination of alkylation reactor in which both alkylation and distillation occurs and a second fractionator operating with the alkylator as one distillation unit; thus unreacted vapour reactants are recovered from the top of the alkylator and the desired product is recovered from the bottom of the second fractionator.

The alkylation process of the present invention may be applied not just for the petrochemical production of alkylation products, e.g. ethylbenzene and cumene, from pure reactants but may also find use in the removal of benzene from gasoline products. Currently the level of benzene in gasoline is of wide-spread environmental concern, and legislation continues to set more rigorous limits on the gasoline specifications. In one aspect of the process of the invention, gasoline products are subjected to alkylation with a source of ethylene and/or propylene, for example refinery gases, fuel gases and any plant off-gases which contain C2 to C4 olefins, in order to remove benzene as alkylaromatic product. This may conveniently be carried out in fixed bed liquid phase alkylation or by catalytic distillation.

When used in the process of the invention the delayered oxide material may be used alone or in combination with a binder, a material which is resistant to the alkylation conditions and acts as a support. Such materials are well known in the art and include refractory oxides such as clays, alumina, silica and silica-alumina. The catalyst may be used in the form of pellets in which the oxide material, plus optional binder, in the form of powder, granules or small particles are compressed and pressed together into larger pellets, or may be used in the form of extrudates, wherein the oxide material and optional binder and/or extrusion aids, are extruded at elevated temperature under high shear pressure. Such techniques are very well known in the art.

Where a multiple bed alkylation reactor is used then the delayered oxide material may be used in all beds or in a mixed catalyst system conjunction with zeolitic alkylation catalysts, such as ZSM-5, zeolite Y and MCM-22 or closely related forms thereof.

Catalyst regeneration may be carried out by any conventional system.

The present invention will now be illustrated by the following Examples.

EXAMPLE 1

Preparation of Oxide Material

First a zeolite precursor of the MWW-type structure, in this case MCM-22(P), which consists of inorganic layers connected together by a layer of organic template material (hexamethyleneimine or HMI) was synthesized in conventional manner. 0.46 g of sodium aluminate (56% $Al_2O_3$, 37% $Na_2O$, Carlo Erba) and 1.62 g of sodium hydroxide (98%, from Prolabo) were dissolved in 203.90 g of distilled water, after which 12.70 g HMI (98%, from Aldrich) and 15.72 g silica (Aerosil 200, from Degussa) were added consecutively. The mixture was stirred vigorously for 30 minutes at room temperature, producing a gel with a silicon to aluminium atomic ratio of 50 (corresponding to a silica to alumina molar ratio of 100). The crystallization of the lamellar precursor was carried out at 408 K (135° C.) over 11 days in a stirred PTFE-lined stainless-steel autoclave under autogeneous pressure. The crystalline product was filtered and washed with distilled water until the pH of the washing water of less than 9 was reached. The material was filtered and dried at 333 K (60° C.) for 12 hours, and showed the XRD characteristic of the laminar precursor of the MWW structure, of the type described in WO 92/11934.

In order to prepare the test zeolite, 10 g of the prepared lamellar precursor were dispersed in 40 g of $H_2O$ milliQ, and 200 g of a cetyltrimethylammonium hydroxide solution (29% wt) and 60 g of a solution of tetrapropylammonium hydroxide (40% wt) were added, giving a final pH of 12.5. The resultant mixture was heated at 353 K (80° C.), stirring vigorously, for 16 hours in order to facilitate the swelling of the layers of the precursor material. At this point, the suspension was delayered by subjecting the suspension in an ultrasound bath to ultrasound treatment at a frequency of 40 kHz and a power of 50 W over 1 hour to disperse the individual sheets. Then, the pH was decreased to 3.0 by adding HCl (6 M) in order to facilitate the flocculation of the delaminated solid. This was recovered by centrifugation and washed with distilled water. After drying at 333 K (60° C.) for 12 hours, the solid was calcined for 3 hours at 813 K (540° C.) in a flow of gaseous nitrogen and then for 6 hours in air. With this calcination treatment all the organic material was decomposed yielding the delaminated MWW-type zeolite which was identified as having the structural characteristics of ITQ-2 by transmission electron microscopy (TEM) and argon adsorption.

COMPARISON EXAMPLE

A zeolite sample of the MWW structure denoted MCM-22 having a silicon to aluminium atomic ratio of 50, was prepared as described in U.S. Pat. No. 4,954,325.

EXAMPLE 2

Alkylation of Benzene with Ethylene

The ITQ-2 powder prepared in Example 1 was pressed into tablets, which were then crushed and sieved to obtain 0.42–0.25 mm diameter granules. Similarly the MCM-22 sample from the Comparison Example was formed into comparable granules. The resulting catalysts were tested for ethylbenzene synthesis activity using a down-flow fixed bed stainless-steel tubular microreactor, internal diameter 4.1 mm and 172 mm long, equipped with a 1.6 mm (outer diameter) axial Thermowell and heated by a two zone electric furnace. In each case the reactor was charged with 1.7 grams of the test catalyst diluted with SiC of 0.84–0.59 mm particle size in a SiC/zeolite mass ratio of 4.

The reaction conditions used in the catalytic test were 3.5 MPa total pressure, 240° C. temperature, and a benzene to ethylene mole ratio of 8. Under these conditions the reaction takes place as a liquid phase alkylation.

The fresh catalyst was treated at a temperature of 150° C. and an atmospheric pressure of 100 cc/min in a stream of gaseous $N_2$ flowing for 3 hours. After the nitrogen flow was turned off, benzene was fed into the reactor at a rate of 100 ml/hour while the reactor temperature and pressure were increased to the desired reaction conditions noted above. After this, the benzene flow was decreased to 96 ml/hour and finally ethylene was introduced from a mass flow controller at a weight hourly space velocity (WHSV) of 1.66. A small amount of gaseous $N_2$ (5–10 ml/min at standard temperature and pressure) was also introduced in order to aid in controlling pressure.

The liquid effluent samples were collected in a cold trap and periodically analyzed off-line in a Varian 3400 GC (gas chromatograph) analyzer.

The results of the alkylation of the ITQ-2 material of the Example and the MCM-22 material of the Comparison Example are shown graphically in FIG. 1 in which it can be clearly seen that the ITQ-2 material provides a consistently higher and relatively constant ethylene conversion of around 75%, against the performance of the MCM-22 sample which leveled at a constant ethylene conversion of approximately 40% after about 1½ hrs from an initial 35% conversion (measured at approximately 30 minutes on stream).

EXAMPLE 3

Alkylation of Benzene with Propylene

ITQ-2 and MCM-22 materials prepared as in Example 1 and the Comparison Example, were also tested utilizing the same equipment and test method in the alkylation of benzene with propylene to form cumene.

The reaction conditions in this test were 3.5 MPa total pressure, 220° C. temperature and a benzene to propylene molar ratio of 6. The reaction was carried out using a propylene flow giving a WHSV of 3.8, and repeated (with fresh catalysts) with the propylene flow adjusted to give a WHSV of 7.6.

Figure 2:
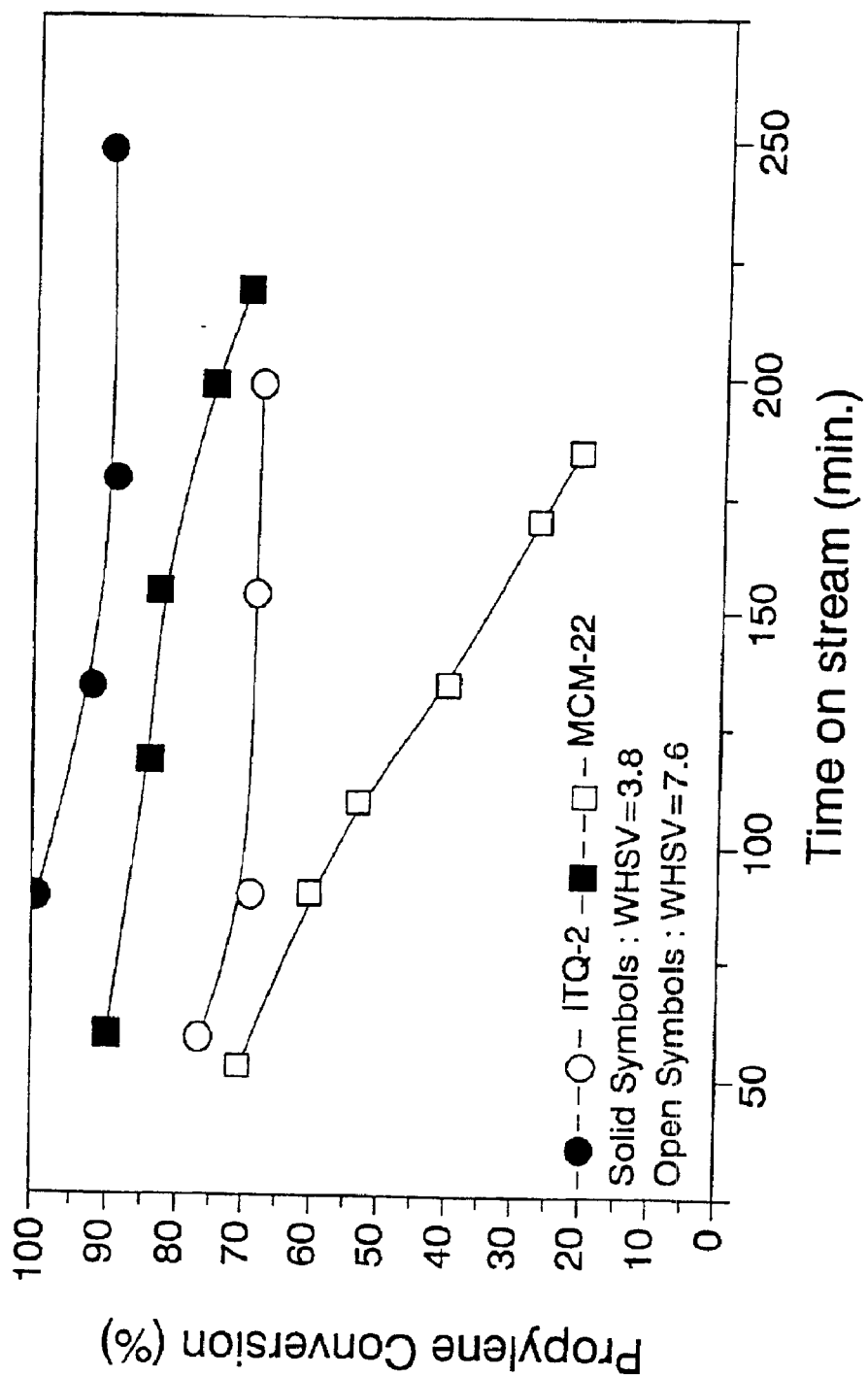

The results from this series of tests are shown in FIG. 2. Again the ITQ-2 material shows a higher conversion activity with a greater conversion consistency over time than the MCM-22 comparison material. The steep drop in activity for the comparison materials for each test WHSV shows that the materials are becoming deactivated; for the WHSV of 7.6 this is particularly marked. In contrast, over the same time on stream the material of Example 1 shows a maintained activity level which shows little catalyst deactivation. The alkylation with MCM-22 ceased early because of excessive catalyst deactivation; the alkylation with ITQ-2 was continued for longer with little catalyst deactivation recorded.

What is claimed is:

1. A process for the alkylation of an aromatic compound with an olefin alkylation agent which comprises contacting the aromatic compound with the olefin alkylation agent in the presence of a catalyst comprising a calcined oxide material which is a delayered MWW zeolite to produce an alkylated aromatic compound.

2. A process as claimed in claim 1, wherein at least 50% of the calcined oxide material comprises single layer material.

3. A process as claimed in claim 2, wherein the delayered zeolite has been obtained by delamination, prior to calcination, of a swollen intermediate material or an as-synthesised material of the MWW-type structures PSH-3, SSZ-25, ERB-1, ITQ-1, or MCM-22.

4. A process as claimed in claim 3, wherein the swollen intermediate material comprises a template being hexamethyleneimine, or a source of adamantane quaternary ammonium ions, or a mixture thereof.

5. A process as claimed in claim 1, wherein the delayered oxide material is characterised in its calcined form as a microporous structure of channels formed by 10-membered atomic rings having a pore diameter of 0.56 nm (5.6 Å) and chalice-shaped cavities that measure 0.8×0.7 nm (8×7 Å) which are open to the outside via 12-membered atomic rings and an adsorption capacity for 1,3,5-trimethylbenzene at a temperature of 42° C. and a pressure of 173.3 Pa of at least 0.50 mmol/g.

6. A process as claimed in claim 1, wherein the aromatic compound is benzene and the olefin alkylation agent is ethylene, propylene or a mixture thereof.

7. A process as claimed in claim 6, which is carried out in liquid phase operation at a temperature in the range of from 150 to 250° C., a pressure in the range of from 3 to 5 MPa, a benzene to olefin molar ratio in the range of from 2:1 to 10:1, and a weight hourly space velocity in the range of from 1 to 10.

8. A process as claimed in claim 7, which is carried out in a fixed bed reactor, or a fixed bed reactor system.

9. A process as claimed in any claim 6, which is the production of cumene from propylene and benzene.

10. A process as claimed in claim 7, which is carried out in a catalytic distillation reactor system.

11. A process as claimed in claim 8, in which one or more beds of said fixed bed reactor or reactor system contain a catalyst comprising ZSM-5, zeolite Y, MCM-22, a zeolite having an MWW structure, or a mixture thereof.

* * * * *

UNITED STATES PATENT AND TRADEMARK OFFICE
CERTIFICATE OF CORRECTION

PATENT NO. : 6,855,855 B2 Page 1 of 1
APPLICATION NO. : 10/102512
DATED : February 15, 2005
INVENTOR(S) : Peter John Van Den Brink et al.

It is certified that error appears in the above-identified patent and that said Letters Patent is hereby corrected as shown below:

Please add on the title page (30) under the heading "Foreign Application Priority Data" the following application:

--European Application No. 99307421.0, filed September 20, 1999--

Signed and Sealed this

Fifth Day of February, 2008

JON W. DUDAS
*Director of the United States Patent and Trademark Office*